United States Patent
Imamura et al.

(10) Patent No.: US 7,214,393 B2
(45) Date of Patent: May 8, 2007

(54) ANTI-ALLERGY COMPOSITION COMPRISING WOOD VINEGAR- OR BAMBOO VINEGAR-DISTILLED SOLUTION

(75) Inventors: Eiyuu Imamura, Yamanashi (JP); Yasuo Watanabe, 12-3, Nakamura-minami 2-chome, Tokyo, Nelima-ku (JP) 176-0025

(73) Assignees: Yamanashiyagen Corporation, Yamanshi, Higashi-Yamanshi-gun (JP); Yasuo Watanabe, Tokyo, Nelima-ku (JP)

( * ) Notice: Subject to any disclaimer, the term of this patent is extended or adjusted under 35 U.S.C. 154(b) by 0 days.

(21) Appl. No.: 11/015,393

(22) Filed: Dec. 17, 2004

(65) Prior Publication Data

US 2005/0136133 A1  Jun. 23, 2005

(30) Foreign Application Priority Data

Dec. 18, 2003  (JP) ............................. 2003-421472

(51) Int. Cl.
  *A61K 36/899* (2006.01)
(52) U.S. Cl. ........................... 424/750; 424/769
(58) Field of Classification Search ............... None
  See application file for complete search history.

(56) References Cited

FOREIGN PATENT DOCUMENTS

JP    2002-226390 A  *  8/2002

OTHER PUBLICATIONS

Japanese Patent Abstract, Publication No. 2000-053973, Feb. 22, 2000, Treatment Of Bamboo Acetic Acid And Device For Treating The Same.
Japanese Patent Abstract, Publication No. 2000-160165, Jun. 13, 2000, Manufacture Of Bamboo Vinegar.

* cited by examiner

*Primary Examiner*—Susan Hoffman
(74) *Attorney, Agent, or Firm*—Rankin, Hill, Porter & Clark LLP

(57) ABSTRACT

The anti-allergy composition of the present invention comprises, as an ineffective ingredient, a wood vinegar-distilled solution. A bamboo vinegar-distilled solution obtained using a bamboo as a wood material is preferable. Also, it is preferable that the present composition does not contain benzopyrene, dibenzanthracene, and methylcholanthrene substantially. The anti-allergy composition can exhibit an anti-allergy effect by oral ingestion. In particular, it is useful for inhibiting Type I allergy such as allergic rhinitis, hay fever, allergic conjunctivitis, atopic dermatitis, allergic asthma, urticaria, food allergy, and anaphylaxis. In addition, the composition can be also applied to a skin. When a wood is subjected to smoking treatment at 130 to 170° C., dried, and then carbonized at 350 to 450° C., a smoke discharged during this carbonization treatment is condensed to obtain a crude wood vinegar, and then the crude wood vinegar is distilled at a low temperature of 50 to 60° C. under reduced pressure to obtain a wood vinegar-distilled solution.

14 Claims, No Drawings

ANTI-ALLERGY COMPOSITION COMPRISING WOOD VINEGAR- OR BAMBOO VINEGAR-DISTILLED SOLUTION

RELATED APPLICATIONS

This application claims priority to the Japanese Patent Application No. 2003-421472 dated on Dec. 18, 2003 and is hereby incorporated with reference for all purposes.

FIELD OF THE INVENTION

The present invention relates to an anti-allergy composition and, in particular, to an anti-allergy composition comprising a wood or bamboo vinegar as an effective ingredient.

BACKGROUND OF THE INVENTION

A bamboo is a plant which has been deeply associated with a life of Japanese from the ancient times. Now, a bamboo thicket is abnormally growing, and is threatening environment in various districts. For this reason, an attempt has been tried to effectively utilize this bamboo as a bamboo charcoal or the like. That is, a moso bamboo (*Phyllostachys heterocycla*) grown in Japan which has been cut into about 50 cm in length is heated in a space of a closed kiln for bamboo at a temperature of 800° C. or higher, and is carefully carbonized over a period of time, thereby, a bamboo charcoal of high quality can be obtained.

Thereupon, the bamboo is thermally cracked, and a bamboo charcoal leaves with a burnt smell smoke. The bamboo charcoal can be appropriately utilized not only as a fuel, but also as various absorbents or deodorants, or a construction material which is laid on wall surfaces or floor surfaces. On the other hand, the smoke is a mixture of gas and water steam containing a variety of components released from a bamboo by thermal cracking. When this water steam is cooled and recovered, it is separated into a water-soluble liquid and an oily liquid. Among them, the former is crude bamboo vinegar, and the latter is tar matter.

A main component of the bamboo vinegar is acetic acid, but the components is complicated. That is, when water occupying 80% to 90% of the whole is removed, the largest amount of a component is acetic acid, a content thereof is about 3.7%. In addition, minor components containing about 200 or more kinds of compounds are dissolved in the bamboo vinegar. More particularly, when water is removed, main components are composed of organic acids such as acetic acid, propionic acid, and formic acid, alcohols such as methanol, propanol, and ethanol, phenols such as 2-methoxyphenol (guaiacol), and cresol, and neutral substances such as valeric acid ester, as well as carbonyl compounds and base components.

Like this, in addition to acetic acid, various components which are useful in a living body, such as polyphenols and organic acids are contained in a bamboo vinegar, and medicinal benefits can be expected by taking them.

However, a bamboo vinegar contains a cancerogenic substance such as benzopyrene, and other harmful substances such as cresol, formaldehyde, formic acid, and methanol. Therefore, although a bamboo vinegar is used in the agricultural and horticultural, and civil engineering fields by diluting with water for the purpose of disinfection, antibacterial treatment, smell removal, deodorization, harmful insect repellency, and cell activation, it has not been actually used in food utility. For this reason, effect of a wood vinegar or a bamboo vinegar by oral ingestion, for example, effect on an allergy reaction has not been tested yet. In recent years, there is a tendency that an increasing number of people suffer from allergy year and year, and safe improvement or prevention of allergy is strongly desired.

As a method of removing a harmful substance from a bamboo vinegar, Japanese Patent Unexamined Publication No. 2000-53973 describes a method of heating a bamboo vinegar at 40 to 50° C., removing formaldehyde and acetone under reduced pressure, and distilling and condensing the residual solution at 60° C. or higher to obtain a bamboo vinegar.

In addition, Japanese Patent Unexamined Publication No. 2000-160165 describes that a bamboo vinegar is adjusted to pH 9 to 11, and aerated with a carbonic gas to pH 6.5 to 7 to remove separated hydrophobic tar matter. Then, this is distilled at 60 to 80° C. under reduced pressure to remove harmful components such as methanol, phenols, and cresol, and then the residual solution, which is adjusted to pH 2.5 to 3, distilled at 80 to 100° C. under reduced pressure to obtain bamboo vinegar as a distilled solution containing acetic acid as a main component.

However, it can not be said that removal of cancerogenic substances such as benzopyrene, dibenzanthracene and methylcholanthrene, and other harmful substances such as cresol or the like is sufficient through these methods, and anti-allergy action by oral ingestion has not been known. And, such problem was also similar in a wood vinegar.

SUMMARY OF THE INVENTION

The present invention was done in view of the aforementioned problems of the prior art, and an object of the present invention is to provide a highly safe anti-allergy composition comprising a wood vinegar or a bamboo vinegar as an effective ingredient, which can be orally ingested.

As a result of diligent studies of the inventors, it has been found that when a bamboo vinegar-distilled solution prepared by a certain method is used as an effective ingredient, an anti-allergy composition that does not substantially contain cancerogenic substances and harmful substances and inhibits an allergy reaction by oral ingestion or by a direct action on cells can be obtained, thereby accomplishing the present invention.

Namely, an anti-allergy composition in accordance with the present invention comprises, as an effective ingredient, a wood vinegar-distilled solution.

In the present invention, it is preferable that said wood vinegar-distilled solution is a bamboo vinegar-distilled solution obtained from a bamboo.

Also, it is preferably that the anti-allergy composition of the present invention does not substantially contain benzopyrene, dibenzanthracene, and methylcholanthrene. The anti-allergy composition of the present invention is preferable for oral ingestion or application on a skin.

A food, beverage, or composition for applying on a skin of the present invention comprises any of said anti-allergy compositions.

A method for inhibiting or preventing an allergy in accordance with the present invention comprises administering an effective amount of any of said anti-allergy compositions by oral ingestion or by a direct action on cells.

In the method of the present invention, it is preferable that said allergy is Type I allergy.

A method for producing a wood vinegar-distilled solution in accordance with the present invention comprises steps of:
  subjecting a wood to smoking treatment at 130 to 170° C.;
  drying the smoking treated wood;

carbonizing the dried wood at 350 to 450° C.;

condensing a smoke discharged during the carbonization treatment to obtain a crude wood vinegar; and distilling the crude wood vinegar at a low temperature of 50 to 60° C. under reduced pressure to obtain a wood vinegar-distilled solution.

In the method for producing a wood vinegar-distilled solution, it is preferable that said wood is a bamboo.

The anti-allergy composition of the present invention contains a distilled solution of a wood vinegar or a bamboo vinegar as an effective ingredient, and can inhibit allergy reaction, in particular, Type I allergy reaction by oral ingestion. Accordingly, it is useful for improving or preventing allergic rhinitis, hay fever, allergic conjunctivitis, atopic dermatitis, allergic asthma, urticaria, food allergy or the like. In addition, the composition can be also applied to a skin. Furthermore, since the distilled solution of a wood vinegar or a bamboo vinegar contains large amount of polyphenols, an effect in a liver disease or an adult disease such as arteriosclerosis and diabetes can be expected. Since the anti-allergy composition of the present invention does not substantially contain benzopyrene, dibenzanthracene and methylcholanthrene which are cancerogenic substances, and a harmful substance such as cresol are scarcely mixed therein, the composition has very high safety, and can be orally ingested over a long period of time.

BEST MODE FOR CARRYING OUT THE INVENTION

When a wood is subjected to smoking treatment at 130 to 170° C., dried, and then carbonized at 350 to 450° C., a smoke discharged during this carbonization treatment is condensed to obtain a crude wood vinegar, and then the crude wood vinegar is distilled at a low temperature of 50 to 60° C. under reduced pressure to obtain a wood vinegar-distilled solution, which is an effective ingredient of the anti-allergy composition of the present invention, for example.

A process for preparing a bamboo vinegar-distilled solution using a bamboo material as a raw material wood will be explained. A bamboo used as a raw material is not particularly limited, but moso bamboo (*Phyllostachys heterocycla*), madake bamboo (*Phyllostachys bambusides*), henon bamboo(*Phyllostachys nigra*), and other bamboos can be used alone, or in combination thereof. Moso bamboo which grows naturally in Minobe-cho, Minamikoma-gun, Yamanashi prefecture in Japan is particularly suitable.

First, a bamboo material used as a raw material is cut and split using an electric saw or the like, placed in a burning kiln, and then subjected to smoking treatment. A temperature of this smoking treatment is 130 to 170° C., preferably 140 to 160° C. The number of treating days is 3 to 7 days, preferably 4 to 6 days. By such smoking treatment, a bamboo vinegar containing a very small amount of a harmful tar matter is obtained at a later stage of collecting a bamboo vinegar. A smoke discharged from a chimney at smoking treatment is not daringly recovered. Generally, carbonization treatment is performed without such pretreatment step in a kiln for smoking, but if this smoking step is not adopted, the bamboo vinegar-distilled solution contains large amount of harmful components.

A smoking-treated bamboo material is dried, and then subjected to carbonization treatment. Carbonization treatment is preferably performed in an earth kiln. A temperature of carbonization treatment is 350 to 450° C., and it is preferable that carbonization is performed slowly over 5 to 15 days.

During this carbonization treatment, a smoke is discharged from a chimney (a chimney made of an acid-resistant material such as stainless steel is used), and this smoke is condensed and dropped down. This droplet is conveniently recovered into a container and the like to obtain a bamboo vinegar. Although this bamboo vinegar contains little tar matter, it is more desirable to separate a small amount of a tar matter from the bamboo vinegar, for example, by allowing to stand for one year or longer.

The bamboo vinegar from which a tar matter has been separated and removed like this is distilled under reduced pressure using a rotary evaporator equipment or the like, thereby, a bamboo vinegar-distilled solution of the present invention can be obtained. That is, in order to prepare a bamboo vinegar-distilled solution, the aforementioned bamboo vinegar may be warmed under reduced pressure. By setting the warming temperature at 50 to 60° C., which is lower than the previous temperature, a cancerogenic substance content can be suppressed low. As a method of reducing a pressure, it is desirable that, first, a pressure is reduced to a certain pressure (e.g. about 130 hPa) while warming at 50° C. to 60° C. and, thereafter, the pressure is gradually decreased (e.g. every 5 hPa) to around 70 hPa while maintaining the temperature. And, it is preferable that collecting a distilled solution (collection of components volatilized by distillation) is performed under reduced pressure at 70 to 110 hPa.

Also under the aforementioned reduced pressure condition, it is more desirable to collect a bamboo vinegar-distilled solution while confirming that a harmful substance such as benzopyrene which is a cancerogenic substance is not mixed therein. A pressure decreasing rate can be adjusted as the occasion demands.

Since a bamboo vinegar-distilled solution obtained by distillation purification like this has very strong acidity, it is desirable to use an acid-resistant container such as a glass bottle as a storage container.

Since thus obtained bamboo vinegar-distilled solution as such has strong peculiar smell or acidic taste, it is difficult to ingest it in some cases. For this reason, the known beverages and foods, or oral preparations such as capsules, tablets, and syrups with a bamboo vinegar-distilled solution added thereto is preferable upon ingestion. Examples of a form include liquid, semi-solid, solid, jelly, cream, mouse and paste, and any of them can be prepared by a conventional method.

For example, by adding 100 to 300 L of water or a fruit juice (apple, grape etc.), or a solution of an aloe or Houttuynia cordata to 1 L of a bamboo vinegar-distilled solution and performing filtration, dreg suction filtration, and charging into a bottle by a conventional method, a highly safe bamboo vinegar beverage having no mixed cancerogenic substance such as benzopyrene and other harmful substance can be obtained. Saccharides such as sugar, oligosaccharide and honey, perfume, and other components which can be usually blended in beverage can be added to such beverages, if necessary.

In the present invention, food or beverage,includes so-called healthy beverage or food, functional beverage or food, and supplement.

In addition, since the anti-allergy composition of the present invention also does not contain components harmful to a skin, it can be also used for a composition applied on a skin such as cosmetics without fear.

Since the anti-allergy composition of the present invention does not contain a cancerogenic substance or a harmful substance which is problematic in oral ingestion or application on a skin, it can be applied over a long period of time. For example, benzopyrene, dibenzanthracene and methylcholanthrene which are cancerogenic substances are not detected also in high performance liquid chromatography analysis having a detection limit of 0.05 ppb, thus the present composition does not contain them substantially.

The anti-allergy composition of the present invention can inhibit Type I allergy reaction by oral ingestion or application on a skin. Examples of such the allergy include allergic rhinitis, hay fever, allergic conjunctivitis, atopic dermatitis, allergic asthma, urticaria, food allergy and anaphylaxis.

An ingestion amount of the anti-allergy composition is appropriately determined according to symptom, sex and the like. Usually, as an amount of a bamboo vinegar-distilled solution, 0.1 to 5 ml per day is suitable for an adult having a weight of 60 kg.

The bamboo vinegar-distilled solution has been explained, but the forgoing can be also applied to a wood vinegar-distilled solution using various woods other than a bamboo as a raw material.

The present invention will be explained in more detail by way of Examples, but the present invention is not limited thereto.

EXAMPLE 1

Preparation of Bamboo Vinegar-distilled Solution

1. Preparation of Crude Bamboo Vinegar:
(1) A naturally grown and from five to six years old moso bamboo which has been grown well in winter at Minobecho, Kuma-gun, Yamanashi prefecture in Japan was cut down, split into 50 cm with an electric saw, and banded together.
(2) This banded bamboo was placed into a smoking kiln, and smoking-treated at a temperature of 150° C. for about 5 days. Thereupon, a smoke discharged from a chimney was not recovered on purpose. Generally, there is no step of placing into a smoking kiln, and all is used for a bamboo vinegar. However, without this step, the obtained bamboo vinegar-distilled solution contains large amount of harmful components. This smoking-treated bamboo material was aged for about 6 months while exposing to the open air in a place where the bamboo material was not exposed to the rain, for drying and stabilizing components.
(3) The bamboo material was placed into an earth kiln, and slowly smoking-carbonized at a low temperature of about 400° C. for 10 days, thereby, a bamboo charcoal product was obtained. A smoke discharged during making of this product was recovered as a water droplet discharged from a stainless chimney to obtain a smoked solution.
(4) Since this smoked solution contained a small amount of a tar matter, it was allowed to stand in a stainless steel tank in a cold and dark place for about 1 year to separate a tar matter and a crude bamboo vinegar, and a supernatant part was recovered as a crude bamboo vinegar.

2. Distillation Purification of Crude Bamboo Vinegar:

The crude bamboo vinegar which was separated as a supernatant part was distilled and purified by the following method.

Equipment Used; Rotary Evaporator

Purification Method; Reducing Method
(a) 2.5 Liter of a crude bamboo vinegar was warmed in a rotating flask (temperature was 50° C. to 60° C.; this temperature was maintained also in later steps).
(b) A pressure in the flask was reduced to 130 hPa.
(c) A pressure was decreased to 115 hPa every 5 hPa (distillation was performed from 130 to 115 hPa for 60 minutes).
(d) A distilled solution at 130 hPa to 115 hPa was not recovered.
(e) Distillation was performed while decreasing the pressure from 115 hPa to 70 hPa by 5 hPa.
(f) During 110 hPa to 70 hPa (distillation time was 140 minutes), a distilled solution (volatile components) was recovered.
(g) After distillation is completed, the pressure was returned to atmospheric pressure, and the distilled solution was taken out to obtain a bamboo vinegar distilled-solution.

The bamboo vinegar-distilled solution obtained as described above is colorless and transparent, and has peculiar smoking smell, a specific gravity of 1.010 or lower, pH 2.5, and the ignition residue weight ratio of 0.001% or smaller.

Results of analysis of the bamboo vinegar-distilled solution (200-fold diluted solution with purified water) are shown in Table 1. From this result, it was made clear that the bamboo vinegar-distilled solution does not contain a cancerogenic substance such as methylcholanthrene, dibenzanthracene and benzopyrene, and a harmful substance such as cresol, methanol, acetone, formaldehyde, and formic acid.

TABLE 1

| Tested Item | Result | Detection Limit |
| --- | --- | --- |
| Acetic aid | 0.01 g/100 g[1] | |
| Isovaleric acid | not detected | 10 ppm[*2] |
| Vanillin | not detected | 0.01 g/kg[*3] |
| Acetone | not detected | 5 ppm[*3] |
| Formaldehyde | not detected | 5 ppm[*4] |
| Guaiacol | not detected | 5 ppm[*3] |
| o-Cresol | not detected | 5 ppm[*3] |
| m-Cresol | not detected | 5 ppm[*3] |
| p-Cresol | not detected | 5 ppm[*3] |
| Maltol | not detected | 5 ppm[*3] |
| Isoeugenol | not detected | 0.1 ppm[*3] |
| 3,4-Benzopyrene | not detected | 0.05 ppb[*1] |
| Formic acid | not detected | 0.01 g/100 g[*1] |
| Methanol | not detected | 5 ppm[*2] |
| 3-Methylcholanthrene | not detected | 0.05 ppb[*1] |
| 1,2,5,6-Dibenzanthracene | not detected | 0.05 ppb[*1] |

[*1] measured by high performance liquid chromatography.
[*2] measured by gas chromatography.
[*3] measured by gas chromatograph-mass spectrometry.
[*4] measured by acetylacetone absorptiometry.

EXAMPLE 2

Anti-Allergy Effect of Bamboo Vinegar-distilled Solution (1) Material and Method (a) Mouse A five week-old BALB/c male mouse which had been reared in the SPF atmosphere was used. Also during a test period, the mouse was reared in the SPF atmosphere. A commercially available solid feed and tap water or test water were fed thereto.

(b) Sensitization of Mouse

Anaphylaxis (typical Type I allergy) was induced in the mouse according to a conventional method. As an antigen, egg white albumin (Sigma) was used. Egg white albumin was dissolved in a physiological saline at 10 mg/ml, and potassium alum was added thereto to be 2 mg/ml to obtain an antigen for sensitization. Sensitization was completed by injecting intraperitoneally 0.1 ml of the antigen solution three times every 2 to 3 days, and injecting intramuscularly 0.1 ml of the antigen solution into a hind paw 4 days after the final intraperitoneal injection.

(c) Preparation of Test Water (Test Bamboo Vinegar Water)

A bamboo vinegar water was prepared by 200-fold diluting the bamboo vinegar-distilled solution obtained in Example 1 with purified water, and was used as a test water. This test water was administered to the mouse (freely ingestion of water) at 200 ml/60 kg body weight as a standard amount (1-fold amount), or at a half thereof (half amount). Therefore, the dose of the bamboo vinegar-distilled solution in a test water-administered group (a standard amount group or a half amount group) corresponds to 1 ml/60 kg body weight or 0.5 ml/60 kg body weight, respectively. Tap water was fed to a control group.

(d) Induction Test

One week after completion of sensitization schedule, administration of the test water was started (water was administered for control group), and an induction test was performed at 1, 5, 10 or 14 day from the start of administration. For induction of a reaction, the antibody for sensitization (not containing potassium alum) was used, and 0.05 ml thereof was subcutaneously injected into a flank of the mouse. Immediately before the induction test, Evans' Blue was injected through a tail vein of the mouse at 2 mg/kg body weight.

(e) Evaluation

Two hours after subcutaneous injection of the antigen solution, the mouse was euthanatized by cervical vertebrae dislocation. A skin around the injected location was excised and its inner side was inverted. The area of Evans' Blue infiltrated in the location was measured. A larger area of infiltrated Evans' Blue indicates a stronger allergy reaction.

(2) Results and Discussion

The following Table 2 shows results of measurement of a reaction part (part of infiltrated Evans' Blue) developed by injection of the inducing antigen.

The "C" group in Table 2 is a negative control group, wherein sensitization with egg white albumin is not performed, and the test water is not administered. In the negative control group, even when the inducing antigen is injected, a reaction does not occur.

The "SC" group is a positive control group, wherein sensitization with egg white albumin is performed, but normal tap water is given. During the test period, infiltration of Evans' Blue was observed, and it was thought that a strong reaction has occurred.

The "½" group in Table 2 shows a group to which a half amount of the test water is administered. In this group, a tendency that infiltration of Evans' Blue was inhibited was recognized, although weak. p The "1/1" group in Table 2 shows a group to which a standard amount of the test water is administered. In this group, by administration for 5 days or longer, inhibition of a reaction was significantly ($p>0.01$) observed as compared with the SC group.

In any test water-administered group, a significant difference in growth (weight gain) of a mouse was not seen as compared with the control group.

TABLE 2

| | Inhibitory effect on Type I allergy in each group (n = 4) | | | |
|---|---|---|---|---|
| Day(s) | C | SC | 1/2 | 1/1 |
| 1 | 0.6 ± 0.3 | 3.6 ± 0.7 | 3.5 ± 0.3 | 3.6 ± 0.8 |
| 5 | 0.7 ± 0.2 | 3.7 ± 0.6 | 3.4 ± 0.4 | 1.8 ± 0.4 |
| 10 | 0.6 ± 0.3 | 4.1 ± 0.5 | 3.8 ± 0.5 | 2.1 ± 0.6 |
| 14 | 0.8 ± 0.4 | 3.8 ± 0.7 | 2.9 ± 0.8 | 1.9 ± 0.8 |

From the foregoing, it can be seen that the anti-allergy composition of the present invention has inhibitory effect on an allergen-inducing allergy, in particular, Type I allergy. IgE antibody intervenes in a reaction of Type I allergy, and it is contemplated that a chemical mediator such as histamine and serotonine contained in a mast cell or a granulocyte plays a main role in the reaction. As Type I allergy, allergic rhinitis, hay fever, allergic conjunctivitis, atopic dermatitis, allergic asthma, urticaria, food allergy, anaphylaxis and the like are known. When the anti-allergy composition of the present invention is ingested, it is expected that such the allergy can be improved or prevented.

EXAMPLE 3

In the following, beverages and foods, or a composition applied on a skin in accordance with the present invention are exemplified.

| Healthy drink | |
|---|---|
| Bamboo vinegar distilled-solution | 10 g |
| Natural water | 900 g |
| Fruit Juice | 90 g |
| Candy | |
| Bamboo vinegar distilled-solution | 5 g |
| Sugar | 200 g |
| Starch syrup | 150 g |
| Water | Q.S. |
| Lotion | |
| Bamboo vinegar distilled-solution | 1 g |
| Glycerin | 10 g |
| Ethanol | 5 g |
| Purified water | 84 g |
| Perfume | Q.S. |

What is claimed is:

1. A method for inhibiting a Type-I allergy comprising administering, by oral ingestion, about 0.1 to about 5 ml per day per 60 kg of body weight of an anti-allergy composition comprising a wood-vinegar distilled solution that is colorless and transparent, and has a specific gravity of no greater than 1.010.

2. The method of claim 1, wherein the wood-vinegar distilled solution is a bamboo-vinegar distilled solution obtained from bamboo.

3. The method of claim 1, wherein the anti-allergy composition contains no greater than 0.5 ppb each of benzopyrene, dibenzanthracene, and methylcholanthrene.

4. The method of claim 1, wherein the anti-allergy composition contains no greater than 5 ppm each of cresol, methanol, acetone, and formaldehyde, and contains no greater than 100 ppm of formic acid.

5. A method for inhibiting a Type-I allergy comprising administering, by oral ingestion, about 0.1 to about 5 ml per day per 60 kg of body weight of an anti-allergy composition comprising a bamboo vinegar-distilled solution obtained from bamboo, wherein the bamboo vinegar-distilled solution is colorless and transparent, and has a specific gravity of no greater than 1.010, and wherein the composition contains no greater than 0.5 ppb each of benzopyrene, dibenzanthracene, and methylcholanthrene.

6. The method of claim 5 wherein the bamboo vinegar-distilled solution contains no greater than 5 ppm each of cresol, methanol, acetone, and formaldehyde, and contains no greater than 100 ppm of formic acid.

7. A method for inhibiting a Type-I allergy comprising administering by oral ingestion, about 0.1 to about 5 ml per day per 60 kg of body weight of a wood vinegar-distilled solution obtained by a method comprising:
   (a) subjecting wood to a smoking treatment at 130° C. to 170° C.;
   (b) drying the treated wood;
   (c) carbonizing the dried wood at 350° C. to 450° C.;
   (d) condensing smoke discharged during the carbonizing to obtain a crude wood vinegar; and
   (e) distilling the crude wood vinegar at 50° C. to 60° C. under reduced pressure to obtain a colorless, transparent wood vinegar-distilled solution having a specific gravity not exceeding 1.010.

8. The method of claim 7 wherein the wood vinegar-distilled solution contains no greater than 0.5 ppb each of benzopyrene, dibenzanthracene, and methylcholantbrene.

9. The method of claim 7 wherein the wood vinegar-distilled solution contains no greater than 5 ppm each of cresol, methanol, acetone, and formaldehyde, and contains no greater than 100 ppm of formic acid.

10. The method of claim 7, wherein the wood is bamboo.

11. The method of claim 7, wherein the pressure in (e) is about 0.07 atm (70 hPa) to about 0.11 atm (110 hPa).

12. The method of claim 10 wherein the bamboo vinegar-distilled solution contains no greater than 0.5 ppb each of benzopyrene, dibeuzanthracene, and methyicholanthrene.

13. The method of claim 10 wherein the bamboo vinegar-distilled solution contains no greater than 5 ppm each of cresol, methanol, acetone, and formaldehyde, and contains no greater than 100 ppm of formic acid.

14. The method of claim 10, wherein the pressure in (e) is about 0.07 atm (70 hPa)to about 0.11 atm (110 hPa).

* * * * *